United States Patent
Ikesu et al.

(10) Patent No.: US 6,204,390 B1
(45) Date of Patent: Mar. 20, 2001

(54) SYNTHESIZING METHOD FOR A 3-SUBSTITUTED-3-OXO-2-(2,4-OXAZOLIDINEDIONE-3-YL) PROPIONIC ACID AMIDE COMPOUND

(75) Inventors: Satoru Ikesu; Kazuhiko Kimura; Katsuji Ota, all of Hino (JP)

(73) Assignee: Konica Corporation, Tokyo (JP)

( * ) Notice: Subject to any disclaimer, the term of this patent is extended or adjusted under 35 U.S.C. 154(b) by 0 days.

(21) Appl. No.: 09/356,633

(22) Filed: Jul. 19, 1999

(30) Foreign Application Priority Data

Jul. 27, 1998 (JP) .................................. 10-225169

(51) Int. Cl.[7] ............................................... C07D 263/04
(52) U.S. Cl. ............................................... 548/226
(58) Field of Search ............................................... 548/226

(56) References Cited

U.S. PATENT DOCUMENTS

| | | | |
|---|---|---|---|
| 4,314,023 | * 2/1982 | Kojima et al. | 430/389 |
| 5,215,877 | * 6/1993 | Sohda et al. | 514/365 |
| 5,665,748 | * 9/1997 | Sohda et al. | 514/365 |

FOREIGN PATENT DOCUMENTS

| | | |
|---|---|---|
| 31 07 173 A1 | 9/1982 | (DE) . |
| 0 475 615 A1 | 3/1992 | (EP) . |
| 0 711 758 A2 | 5/1996 | (EP) . |
| 1 527 851 | 10/1978 | (GB) . |

OTHER PUBLICATIONS

Patent Abstracts of Japan, vol. 199, No. 812, Oct. 31, 1998 of JP 10 186601 A, Jul. 14, 1998.

* cited by examiner

*Primary Examiner*—Floyd D. Higel
*Assistant Examiner*—Sonya R. Wright
(74) *Attorney, Agent, or Firm*—Frishauf, Holtz, Goodman, Langer & Chick, P.C.

(57) ABSTRACT

A synthesizing method for a 3-substituted-3-oxo-2-(2,4-oxazolidinedione-3-yl)propionic acid amide compound represented by the following Formula [I], by reacting a compound represented by the following Formula [II] with a compound represented by the following Formula [III], in the presence of an organic base;

Formula [I]

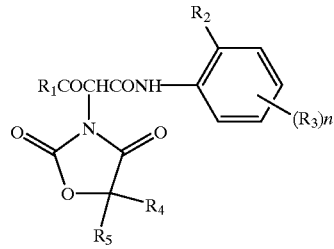

Formula [II]

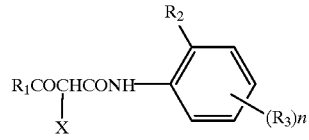

Formula [III]

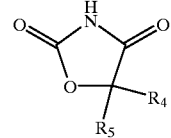

6 Claims, No Drawings

SYNTHESIZING METHOD FOR A 3-SUBSTITUTED-3-OXO-2-(2,4-OXAZOLIDINEDIONE-3-YL) PROPIONIC ACID AMIDE COMPOUND

FIELD OF THE INVENTION

The present invention relates to a synthesizing method for a 3-substituted-3-oxo-2-(2,4-oxazolidinedione-3-yl) propionic acid amide compound.

Said 3-substituted-3-oxo-2-(2,4-oxazolidinedione-3-yl) propionic acid amide compound is an important compound as a yellow coupler used in a silver halide photographic light-sensitive material, or as its intermediate compound, or as an intermediate manufacturing compound for medical compounds.

BACKGROUND OF THE INVENTION

As the synthesizing methods for said 3-substituted-3-oxo-2-(2,4-oxazolidinedione-3-yl)propionic acid amide compound, the following methods are conventionally proposed:

(1) a synthesizing method for obtaining said 3-substituted-3-oxo-2-(2,4-oxazolidinedione-3-yl)propionic acid amide compound by reacting 3-substituted-3-oxo-2-chloropropionic acid amides with potassium salts of 2,4-oxazolidinediones in acetonitrile (described in Japanese Patent Publication Open to Public Inspection (hereinafter referred to as JP-A) No. 48-66835);

(2) a synthesizing method for obtaining said 3-substituted-3-oxo-2-(2,4-oxazolidinedione-3-yl)propionic acid amide compound by reacting the 3-substituted-3-oxo-2-chloropropionic acid amides with the 2,4-oxazolidinediones in the presence of potassium hydroxide (described in JP-A No. 52-115219);

(3) a synthesizing method for obtaining said 3-substituted-3-oxo-2-(2,4-oxazolidinedione-3-yl)propionic acid amide compound by reacting the 3-substituted-3-oxo-2-chloropropionic acid amides with the 2,4-oxazolidinediones in the presence of potassium carbonate (described in JP-A No. 4-124661).

In these conventional synthesizing methods for said 3-substituted-3-oxo-2-(2,4-oxazolidinedione-3-yl)propionic acid amide compound, either a reaction by the use of salts of the 2,4-oxazolidinediones or a reaction in the presence of inorganic base is employed. In the former case, since it is necessary that the salts of the 2,4-oxazolidinediones are previously prepared or isolated, consequently the synthesizing is rather complex.

On the other hand, in the latter case, the reaction in the presence of the inorganic base has an adverse effect such that said reaction is accompanied by unpreferable side reactions, specifically in the later synthesizing processes, and consequently the reaction yield is lowered.

SUMMARY OF THE INVENTION

Accordingly, an object of the present invention is to provide a synthesizing method for a 3-substituted-3-oxo-2-(2,4-oxazolidinedione-3-yl)propionic acid amide compound at a high yield, as well as ease in synthesizing it.

DETAILED DESCRIPTION OF THE INVENTION

The above-mentioned object of the present invention can be attained by the following method:

(1) A synthesizing method for obtaining a 3-substituted-3-oxo-2-(2,4-oxazolidinedione-3-yl)propionic acid amide compound represented by the following Formula [I], by reacting a compound represented by the following Formula [II] with a compound represented by the following Formula [III], in the presence of an organic base;

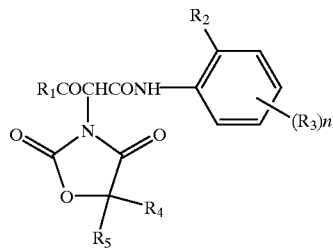

Formula [I]

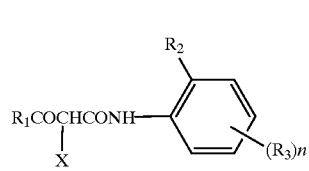

Formula [II]

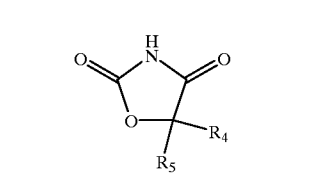

Formula [III]

wherein, $R_1$ represents an alkyl group, a cycloalkyl group, an aryl group, an amino group or a heterocyclic group; $R_2$ represents a chlorine atom, an alkoxy group or an aryloxy group; $R_3$ represents a substituent group; n represents an integer of 0 to 4; when n represents an integer of at least 2, plural $R_3$ may be the same or different; $R_4$ and $R_5$ each represent a hydrogen atom, an alkyl group or an aryl group; while X represents a chlorine atom or a bromine atom.

(2) The synthesizing method for obtaining said 3-substituted-3-oxo-2-(2,4-oxazolidinedione-3-yl)propionic acid amide compound of Item 1, wherein the boiling point of said organic base is between 120° C. –190° C.

(3) The synthesizing method for obtaining said 3-substituted-3-oxo-2-(2,4-oxazolidinedione-3-yl)propionic acid amide compound of Item 1, wherein $R_5$ of said 3-substituted-3-oxo-2-(2,4-oxazolidinedione-3-yl)propionic acid amide compound represented by the Formula [I] is a hydrogen atom.

The present invention will be explained below in detail.

First, the compound represented by Formula [I], Formula [II] and Formula [III] will be explained in detail.

In Formula [I] and Formula [II], examples of an alkyl group represented by $R_1$ include a methyl group, an ethyl group, an iso-propyl group, a t-butyl group and a dodecyl group, etc. These alkyl groups may have a substituent group, and examples of said substituent group include, for example, a halogen atom, an aryl group, an alkoxy group, an aryloxy group, an alkylsulfonyl group, an acylamino group and a hydroxy group, etc.

Examples of a cyclohexyl group represented by $R_1$ include a cyclopropyl group, a cyclohexyl group and an adamantyl group, etc.

As an aryl group represented by $R_1$, can be cited an aryl group having 6 to 14 carbon atoms (for example, a phenyl group, a 1-naphthyl group and a 9-anthranyl group, etc.). Said aryl group represented by $R_1$ can further contain a substituent group, and examples of said substituent group include a nitro group, a cyano group, an amino group (for example, a dimethylamino group and an anilino group, etc.), an alkylthio group (for example, a methylthio group, etc.), the same alkyl group as defined for the above-mentioned $R_1$, and the same substituent group as defined for the substituent group which the alkyl group represented by the above-mentioned $R_1$ can contain.

Examples of an amino group include an unsubstituted amino group and a substituted amino group such as a diethylamino group, a di-iso-octylamino group and an anilino group, etc. These amino groups can further contain a substituent group, and said substituent group includes the same substituent group as defined for the substituent group which the alkyl group represented by the above-mentioned $R_1$ can contain.

Examples of a heterocyclic group represented by $R_1$ include a morpholino group and an indoline-1-yl group, etc.

Examples of an alkoxy group represented by $R_2$ include a methoxy group, an ethoxy group, an iso-propoxy group, a butoxy group, a decyloxy group and a dodecyloxy group, etc., and as an aryloxy group represented by $R_2$, a phenoxy group is representative.

In Formula [I] and Formula [II], $R_3$ represents a substituent group, and any substituent which can substitute on a benzene ring can be used without limitation. Examples of said substituent include the same alkyl group, cycloalkyl group and aryl group as defined for $R_1$, and additionally an alkyl group substituted with a halogen atom (for example, a trifluoromethyl group, etc.), a halogen atom (for example, a chlorine atom, a bromine atom, etc.), a cyano group, a nitro group, an alkenyl group (for example, a 2-propylene group, an oleyl group, etc.), a hydroxy group, an alkoxy group (for example, a methoxy group, a 2-ethoxyethoxy group, etc.), an aryloxy group (for example a phenoxy group, a 2,4-di-tert-amylphenoxy group, 4-(4-hydroxyphenylsulfonyl) phenoxy group, etc.), a heterocyclicoxy group (for example, a 4-pyridyloxy group, a 2-hexahydropyranyloxy group, etc.), a carbonyloxy group (for example, an alkylcarbonyloxy group such as an acetyloxy group, a trifluoroacetyloxy group, a pivaloyloxy group, etc., an aryloxy group such as a benzoyloxy group, a pentafluorobenzoyloxy group, etc.), a sulfonyloxy group (for example, an alkylsulfonyloxy group such as a methanesulfonyloxy group, a trifluoromethanesulfonyloxy group, a n-dodecanesulfonyloxy group, etc., an arylsulfonyloxy group such as a benzenesulfonyloxy group, a p-toluenesulfonyloxy group, etc.), a carbonyl group (for example, an alkylcarbonyl group such as an acetyl group, a trifluoroacetylpivaloyl group, etc., an arylcarbonyl group such as a benzoyl group, a pentafluorobenzoyl group, a 3,5-di-tert-butyl-4-hydroxybenzoyl group, etc.), an oxycarbonyl group (for example, an alkoxycarbonyl group such as a methoxycarbonyl group, a cyclohexyloxycarbonyl group, a n-dodecyloxycarbonyl group, etc., an aryloxycarbonyl group such as a phenoxycarbonyl group, a 2,4-di-tert-amylphenoxycarbonyl group, a 1-naphthyloxycarbonyl group, etc., a heterocyclicoxycarbonyl group such as a 2-pyridyloxycarbonyl group, a 1-phenylpyrazolyl-5-oxycarbonyl group, etc.), a carbamoyl group (for example, an alkylcarbamoyl group such as a dimethylcarbamoyl group, a 4-(2,4-di-tert-amylphenoxy)butylaminocarbonyl group, etc., an aryl carbamoyl group such as a phenylcarbamoyl group, a 1-naphthylcarbamoyl group, etc.), a sulfonyl group (for example, an alkylsulfonyl group such as a methanesulfonyl group, a trifluoromethanesulfonyl group, etc., an arylsulfonyl group such as a p-toluenesulfonyl group, etc.), a sulfamoyl group (for example, an alkylsulfamoyl group such as a dimethylsulfamoyl group, a 4-(2,4-di-tert-amylphenoxy)butylaminosulfonyl group, etc., an arylsulfamoyl group such as a phenylsulfamoyl group, etc.), an amino group (for example, an alkylamino group such as a dimethylamino group, a cyclohexylamino group, a n-dodecylamino group, etc., an arylamino group such as an anilino group, a p-tert-octylanilino group, etc.), a sulfonylamino group (for example, an alkylsulfonylamino group such as a methanesulfonylamino group, a heptafluoropropanesulfonylamino group, a n-hexadecylsulfonylaminio group, etc., an arylsulfonylamino group such as a p-toluenesulfonylamino group, a pentafluorobenzenesulfonylamino group, etc.), an acylamino group (for example, an alkylcarbonylamino group such as an acetylamino group, a myristoylamino group, etc., an arylcarbonylamino group such as a benzoylamino group, etc.), an alkylthio group (for example, a methylthio group, a tert-octylthio group, etc.), an arylthio group (for example, a phenylthio group, etc.), and a heterocyclicthio group (for example, a 1-phenyltetrazole-5-thio group, a 5-methyl-1,3,4-oxadiazole-2-thio group, etc.).

In the above-mentioned Formula [I] and Formula [II], n represents an integer of 0 to 4, and when n represents an integer of at least 2, each of $R_3$ may be the same substituent or a different substituent. Further, in that case, plural $R_3$ may bond with each other to form a ring structure.

In Formula [I] and Formula [III], $R_4$ and $R_5$ each represent a hydrogen atom, an alkyl group or an aryl group, and said alkyl group and said aryl group can represent the same alkyl group and aryl group as defined for those represented by the above-mentioned $R_1$.

In Formula [I] and Formula [III], it is more preferable that $R_5$ represents a hydrogen atom, because the effects of the present invention are more excellently exhibited.

Next, an organic base used in the present invention will be detailed.

As said organic base, for example, are cited triethyl amine (boiling point: 166° C.), pyridine (boiling point: 115° C.), N,N-dimethylaniline (boiling point: 193–194°C.), N,N,N',N'-tetramethyldiaminopropane (boiling point: 145–146° C.), and N,N,N',N'-tetramethyldiaminobutane (boiling point: 166–167° C.).

The boiling point of these bases is preferably not less than 120° C. due to decreased odor and is preferably not more than 190° C. in terms of recovery and reusing.

A compound represented by Formula [I] is preferably synthesized by reacting a compound represented by Formula [II] with a compound represented by Formula [III] using an organic base.

Formula [II]

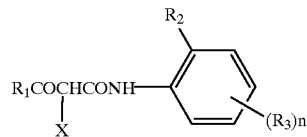

Formula [III]

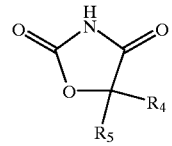

wherein $R_1$ represents an alkyl group, a cycloalkyl group, an aryl group, an amino group or a heterocyclic group; $R_2$ represents a chlorine atom, an alkoxy group or an aryloxy group; $R_3$ represents a substituent group; and n represents an integer of 0 to 4. When n represents an integer of at least 2, plural $R_3$ may be the same or different. $R_4$ and $R_5$ each represent a hydrogen atom, an alkyl group or an aryl group, while X represents a chlorine atom or a bromine atom. In synthesizing the compound represented by Formula [I], with respect to using molar ratio of the compound represented by Formula [III] to the compound represented by Formula [II], 0.8 to 3 mol of the compound represented by Formula [III] is preferably used per mol of the compound represented by Formula [II], while specifically preferable is 1 to 1.5 mol.

In synthesizing the compound of the present invention, a solvent may or may not be used, but it is preferably used. As the kind of said solvent, an aromatic hydrocarbon type solvent, an ether type solvent, an ester type solvent and a nitrile type solvent are preferable, of these, the ester type solvent is specifically preferable.

Reaction temperature is preferably between 20 to 250° C., and is specifically preferably between 60 to 150° C. When the reaction temperature is too low, the reaction speed is extremely slow, and when the reaction temperature is too high, the amount of undesirable by-products increases.

Reaction time depends on the kind of the compound represented by Formula [I], the reaction temperature, the kind and amount of the solvent used, and other reaction conditions, but the reaction time is usually between 1 to 20 hours.

The synthesized compound represented by Formula [I] can be obtained according to a conventional manner in which said synthesized compound is separated from a reaction solution through distillation or recrystallization, after reaction.

Exemplified compounds represented by Formulas [I], [II] and [III] will be shown below, however the present invention is not limited thereto.

[I]-1
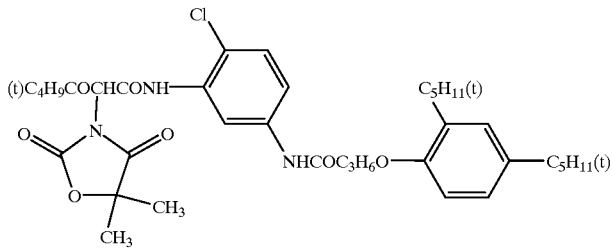

[I]-2
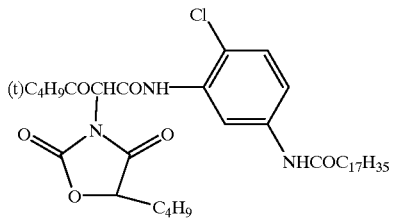

[I]-3
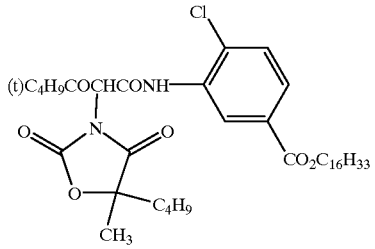

[I]-4
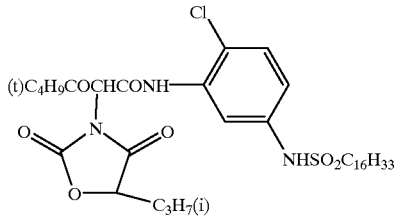

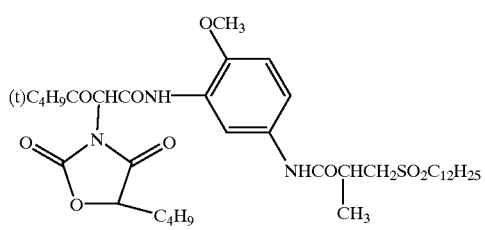
[I]-5
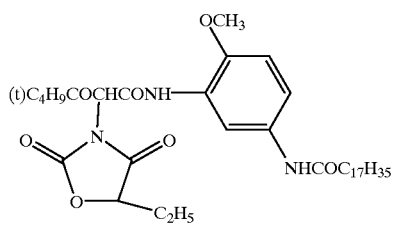
[I]-6
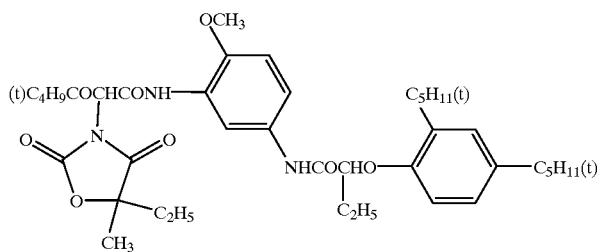
[I]-7
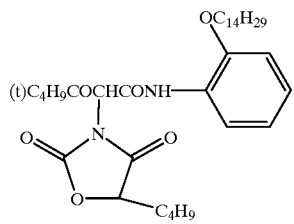
[I]-8
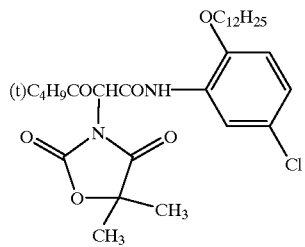
[I]-9
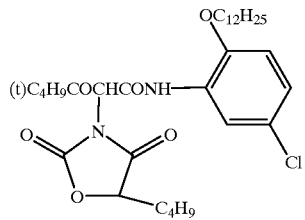
[I]-10

[I]-11
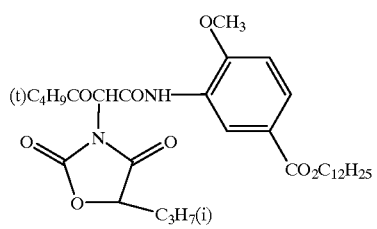
[I]-12
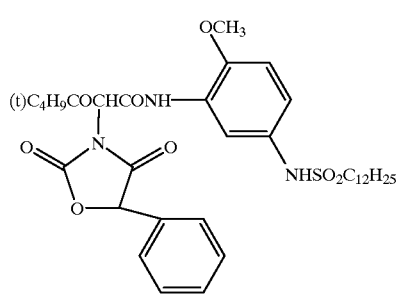
[I]-13
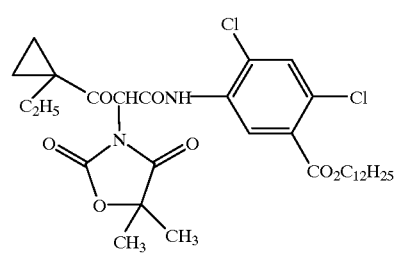
[I]-14
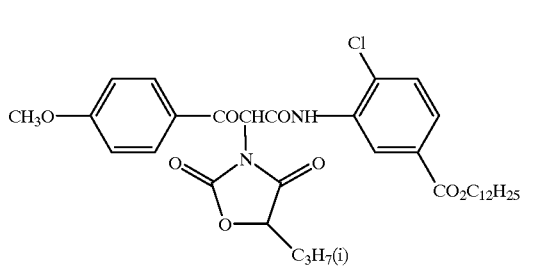
[I]-15
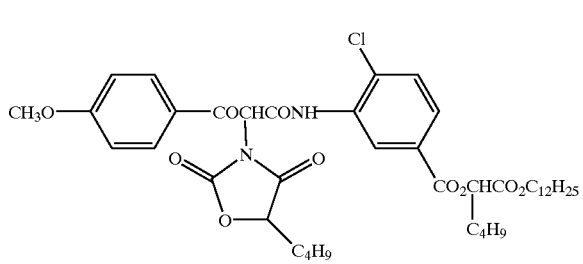
[I]-16
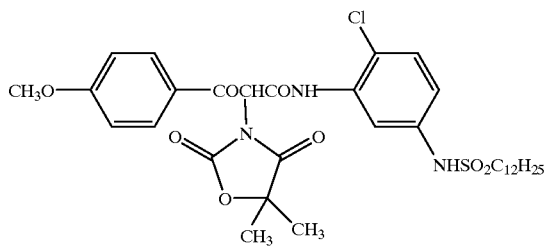

-continued
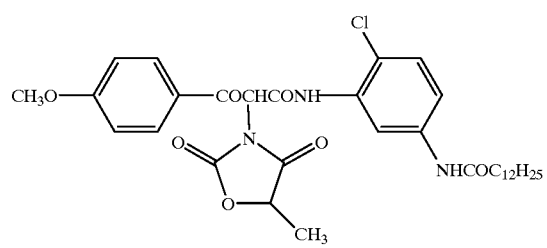
[I]-17
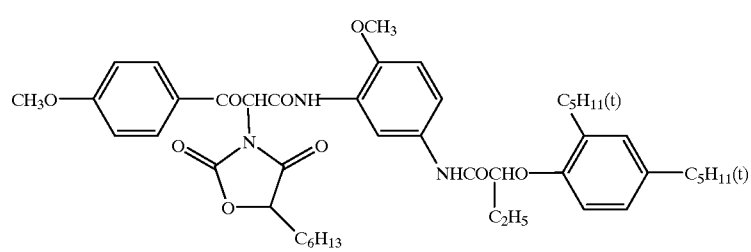
[I]-18
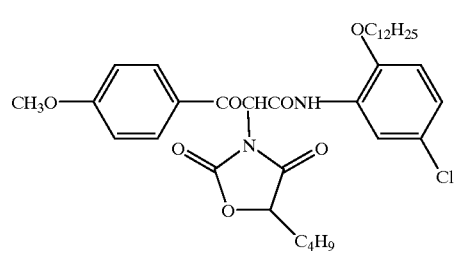
[I]-19
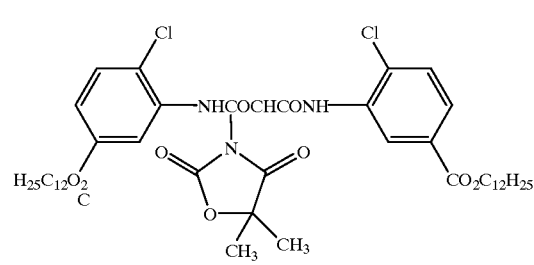
[I]-20
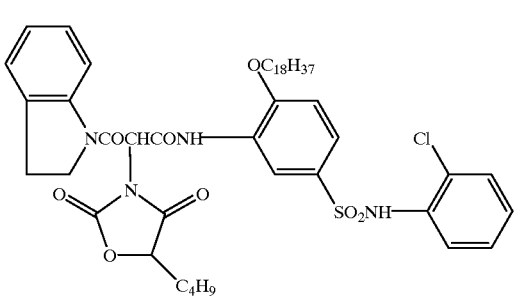
[I]-21
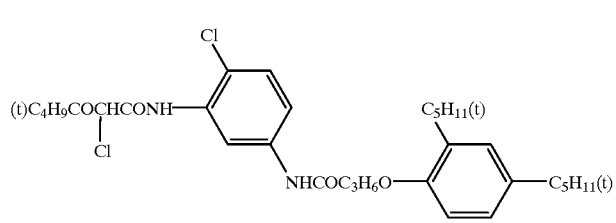
[II]-1

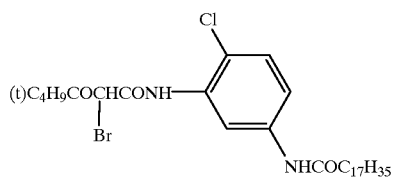 [II]-2
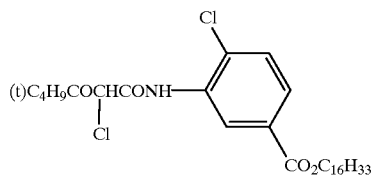 [II]-3
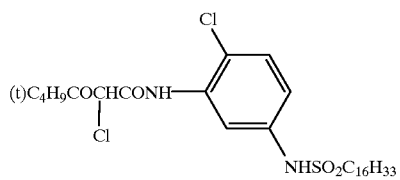 [II]-4
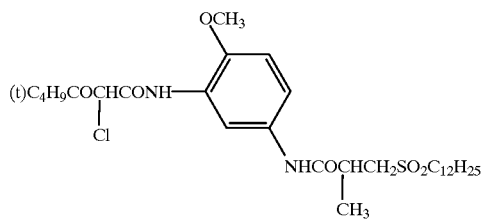 [II]-5
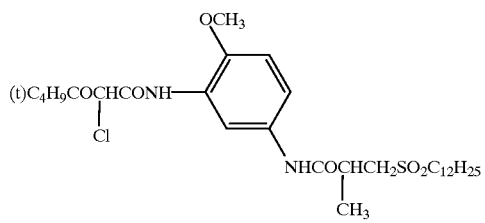 [II]-6
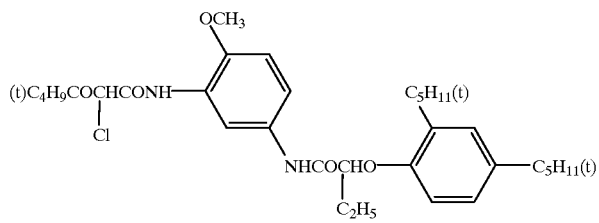 [II]-7
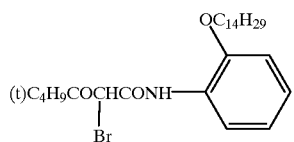 [II]-8

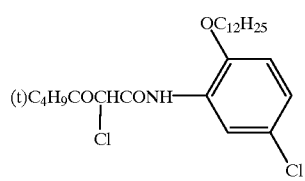  [II]-9
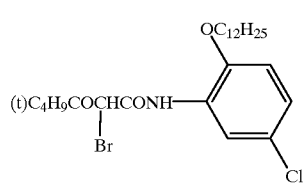  [II]-10
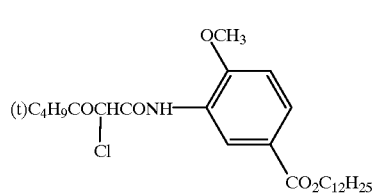  [II]-11
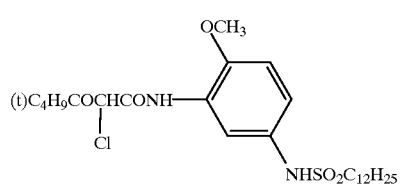  [II]-12
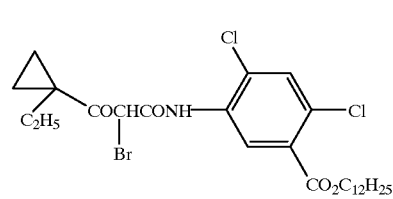  [II]-13
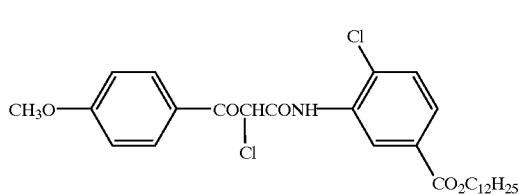  [II]-14
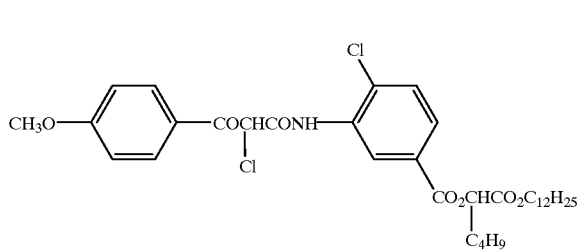  [II]-15
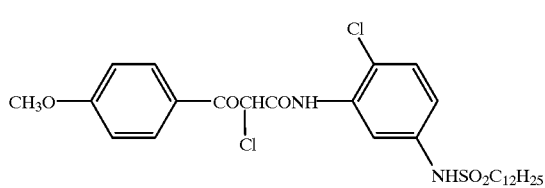  [II]-16

[II]-17
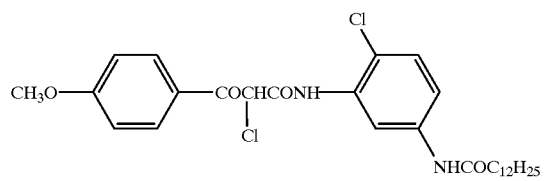
[II]-18
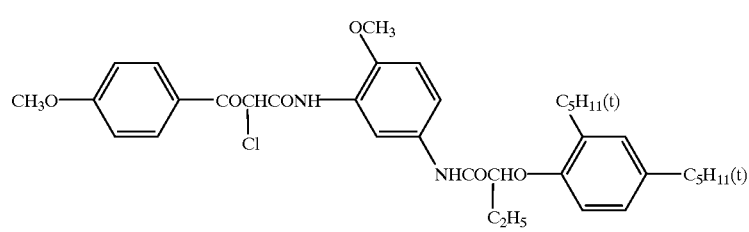
[II]-19
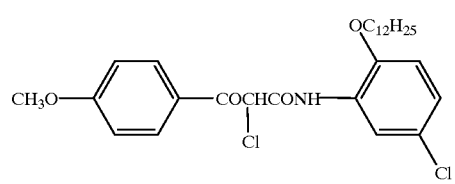
[II]-20
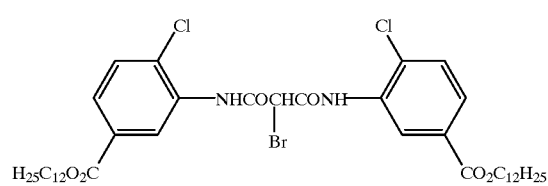
[II]-21
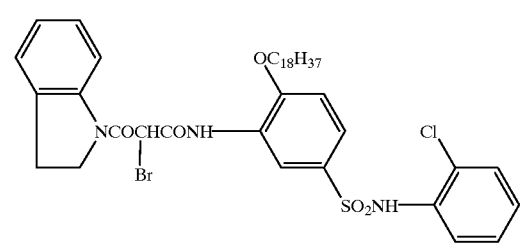
[III]-1
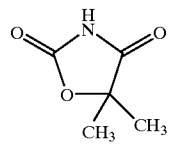
[III]-7
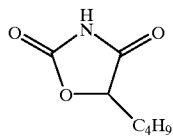
[III]-2
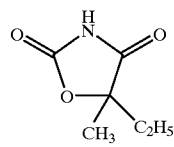
[III]-8
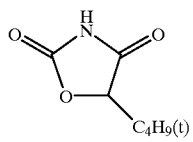
[III]-3
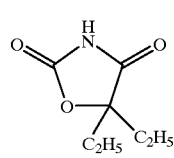
[III]-9
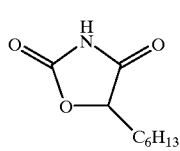

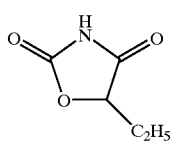
[III]-4

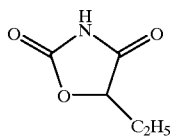
[III]-5

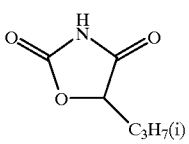
[III]-6

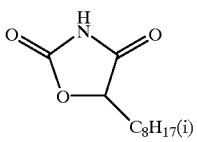
[III]-10

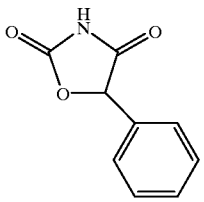
[III]-11

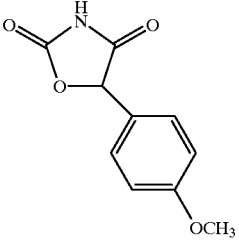
[III]-12

EXAMPLES

The present invention is explained with reference to examples below. However, the present invention is not limited to these examples. (Synthesis of an exemplified compound [II]-9)

The exemplified compound [II]-9 was synthesized according to the following synthesizing scheme.

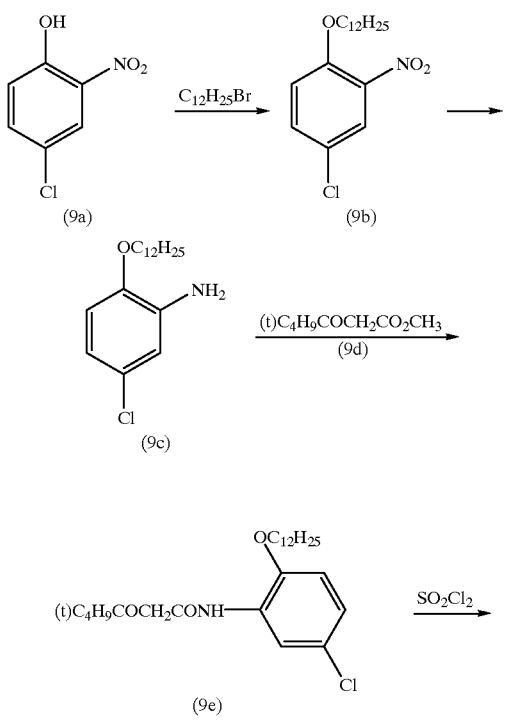

Exemplified compound [II]-9

(i) Synthesis of (9b)

105.3 g (0.607 mol) of a compound (9a) was dissolved in 150 ml of N,N-dimethylformamide and to the thus obtained solution was added 166.3 g (0.667 mol) of dodecylbromide. Further, to the resulting solution was slowly added 62.9 g (0.455 mol) of a fine potassium carbonate powder while the solution was being stirred at room temperature. After that, the reaction temperature of the thus obtained solution was raised from 95 to 100° C. and the solution was stirred for 3 hours to prod the reaction along. After completion of the reaction, the temperature of the reaction solution was cooled down to room temperature, and undissolved substances were filtered out. To the thus obtained filtrate were added 378 ml of ethylacetate and 150 ml of water. After that, the organic phase was separated from the water phase. The water phase was removed to leave the organic phase which was washed twice with 150 ml of a 20% aqueous salt solution, then the organic phase was concentrated under a reduced pressure so as to obtain 223 g of the compound (9b). The thus obtained compound (9b) was employed in the following process without purification.

(ii) Synthesis of a compound (9c)

To 223 g of the compound (9b) obtained above was added 450 ml of methanol and further added 15.6 g of a Raney nickel catalyzer, NDT-65 (produced by Kawaken Chemical Co.), and the thus obtained solution was subjected to hydrogenation under reaction conditions of 10 atmospheric pressure and reaction temperature of 55° C. for 4 hours. After completion of the reaction, the catalyzer was filtered out at 45° C. and washed with 120 ml of methanol at about 50° C. The filtrate was allowed to stand so as to precipitate crystals.

The temperature of the filtrate was cooled down to about 7° C. and precipitated crystals were filtered and washed with 95 ml of cooled methanol so as to obtain 165 g of the compound (9c) at a total yield of 87%, obtained in 2 steps, step (i) and step (ii).

(iii) Synthesis of a compound (9e)

To 434 ml of toluene were added 148 g (0.476 mol) of the compound (9c) and 82.8 g (0.523 mol) of the compound (9d), and the compound (9c) and the compound (9d) were reacted for 14 hours to gradually remove methanol produced in the course of the reaction, and also to gradually remove toluene by distillation. A total of about 300 ml of toluene and methanol was removed by distillation, and a toluene solution containing the compound (9d) was obtained.

(iv) Synthesis of the exemplified compound [II]-9

Into the toluene solution containing the compound (9d), was dripped 63.0 g (0.467 mol) of sulfuryl chloride while maintaining temperature of said toluene solution at about 40° C. After that, by evaporating the solvent under a reduced pressure, 225 g of the exemplified compound [II]-9 was obtained.

The thus obtained exemplified compound could be used in the following step without purification.

Example 1

Synthesis of an exemplified compound [I]-10

To 225 g (0.476 mol) of the exemplified compound [II]-9 synthesized according to the above-mentioned method, were added 150 ml of ethylacetate, 86.0 g (0.547 mol) of an exemplified compound [III]-7 and 55.4 g (0.547 mol) of triethylamine, and the thus obtained mixture was refluxed upon heating for 5 hours so that the exemplified compound [II]-9 reacted completely with the exemplified compound [III]-7. After completion of the reaction, to the mixture obtained above was added 120 ml of water and then an organic phase separated from the water phase was extracted. After that, the organic phase was washed with a diluted aqueous sulfuric acid solution, for neutralization thereof. Furthermore, the organic phase was washed twice with a saturated aqueous salt solution, and then the solvent was evaporated under a reduced pressure. The obtained residue was recrystallized from 480 ml of methanol. Thus, 237 g of the exemplified compound [I]-10 at a total yield of 84%, obtained in a total of 3 steps, step (iii), step (iv) and the present step, was obtained.

The melting point of the exemplified compound [I]-10 was 83–86° C., and the chemical structure of the exemplified compound [I]-10 was confirmed by $^1$H-NMR spectrum, IR spectrum and Mass spectrum.

Example 2

The exemplified compound [I]-10 was obtained in the same manner as employed in Example 1 except for replacing 55.4 g (0.547 mol) of triethylamine with 35.6 g (0.273 mol) of N,N,N',N'-tetramethyldiaminopropane. Thus 243 g of the exemplified compound [I]-10 was obtained (at a total yield of 87%, in a total of 3 steps).

Comparative Example

The exemplified compound [I]-10 was obtained in the same manner as employed in Example 1 except for replacing 55.4 g (0.547 mol) of triethylamine with 75.5 g (0.547 mol) of potassium carbonate. Thus, 218 g of the exemplified compound [I]-10 was obtained (at a total yield of 78%, in a total of 3 steps).

As can be seen by comparing Example 1 and Example 2 with the Comparative Example, the 3-substituted-3-oxo-2-(2,4-oxazolidinedione-3-yl)propionic acid amide compound can be synthesized at a high yield, as well as ease in synthesizing it according to the present inventive synthesizing method.

[Effects of the Invention]

According to the present invention, the 3-substituted-3-oxo-2-(2,4-oxazolidinedione-3-yl)propionic acid amide can be synthesized at a high yield, as well as ease in synthesizing the same.

What is claimed is:

1. A synthesizing method for obtaining a 3-substituted-3-oxo-2-(2,4-oxazolidinedione-3-yl)propionic acid amide compound represented by the following Formula [I], by reacting a compound represented by the following Formula [II] with a compound represented by the following Formula [III], in the presence of an organic base;

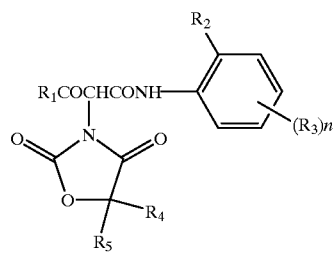

Formula [I]

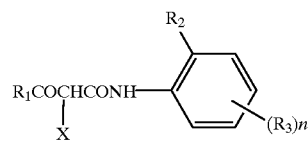

Formula [II]

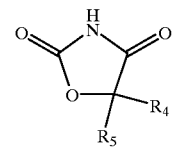

Formula [III]

wherein, $R_1$ represents an alkyl group, a cycloalkyl group, an aryl group, an amino group or a heterocyclic group; $R_2$ represents a chlorine atom, an alkoxy group or an aryloxy group; $R_3$ represents a substituent group; n represents an integer of 0 to 4; when n represents an integer of at least 2, plural $R_3$ may be the same or different; $R_4$ and $R_5$ each represent a hydrogen atom, an alkyl group or an aryl group; while X represents a chlorine atom or a bromine atom.

2. The synthesizing method for obtaining said 3-substituted-3-oxo-2-(2,4-oxazolidinedione-3-yl)propionic acid amide compound of claim 1, wherein the boiling point of said organic base is between 120° C. –190° C.

3. The synthesizing method for obtaining said 3-substituted-3-oxo-2-(2,4-oxazolidinedione-3-yl)propionic acid amide compound of claim 1, wherein $R_5$ of said 3-substituted-3-oxo-2-(2,4-oxazolidinedione-3-yl)propionic acid amide compound represented by the Formula [I] is a hydrogen atom.

4. The synthesizing method for obtaining said 3-substituted-3-oxo-2-(2,4-oxazolidinedione-3-yl)propionic acid amide compound of claim 3, wherein the organic base is selected from a group consisting of triethyl amine, pyridine, N,N-dimethylaniline, N, N, N',N'-tetramethyldiaminopropane, and N,N,N',N'-tetramethyldiaminobutane.

5. The synthesizing method for obtaining said 3-substituted-3-oxo-2-(2,4-oxazolidinedione-3-yl)propionic acid amide compound of claim 1, wherein the organic base is selected from a group consisting of triethyl amine, pyridine, N,N-dimethylaniline, N, N, N',N'-tetramethyldiaminopropane, and N,N,N',N'-tetramethyldiaminobutane.

6. The synthesizing method of claim 5 wherein the compound of formula [II] is selected from the group consisting of compounds of formulas [II]-1 through [II]-21 presented below; and the compound of formula [III] is selected from the group consisting of [III]-1 through [III]-12 presented below:
[II]-1
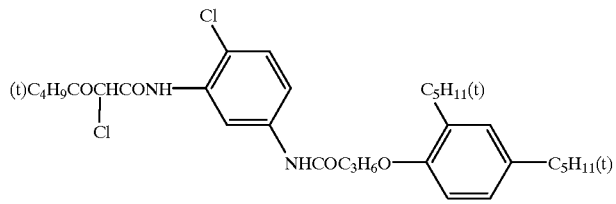
[II]-2
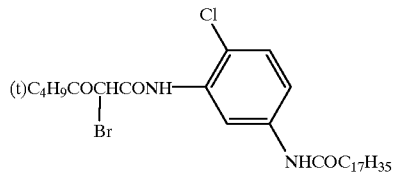
[II]-3
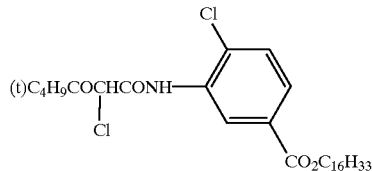
[II]-4
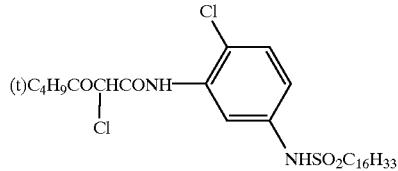
[II]-5
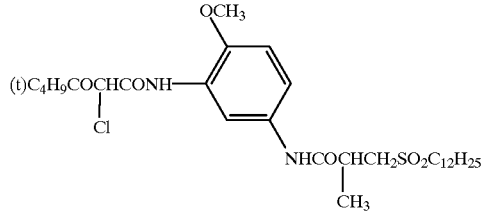
[II]-6
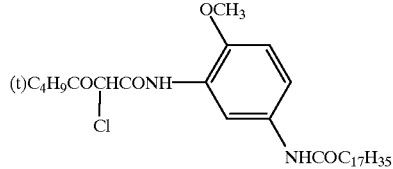
[II]-7
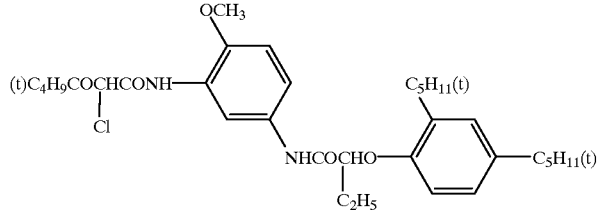

-continued
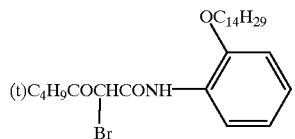
[II]-8
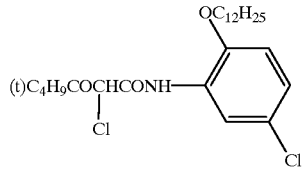
[II]-9
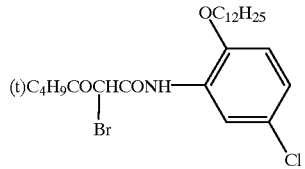
[II]-10
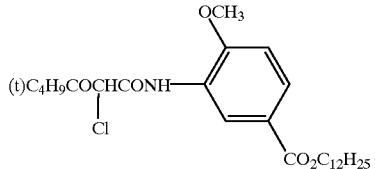
[II]-11
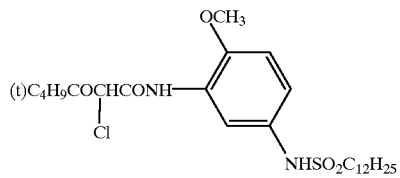
[II]-12
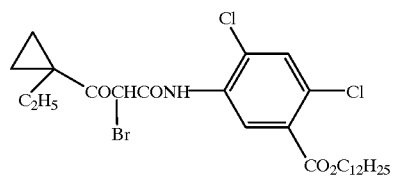
[II]-13
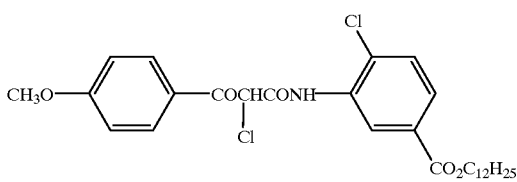
[II]-14
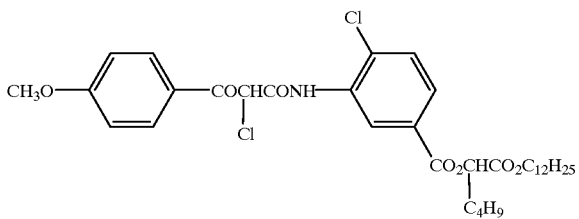
[II]-15

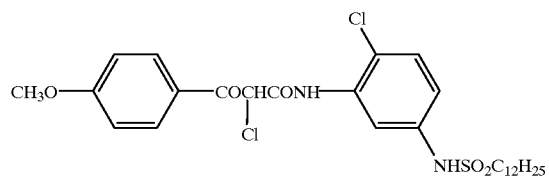
[II]-16
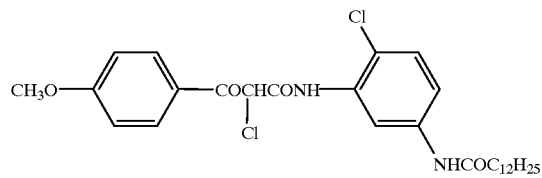
[II]-17
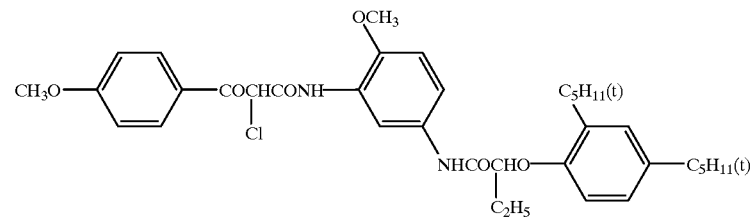
[II]-18
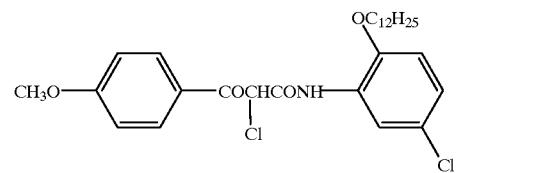
[II]-19
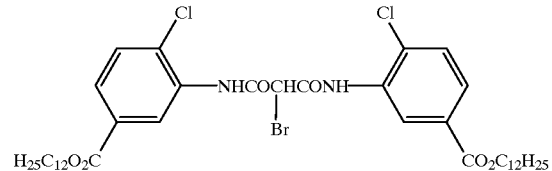
[II]-20
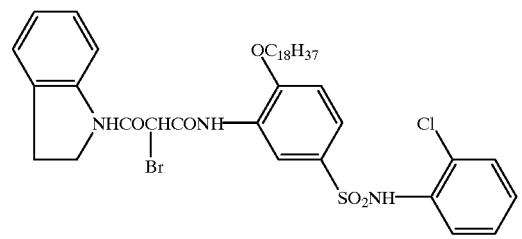
[II]-21
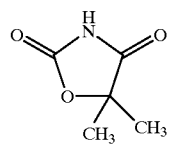
[III]-1
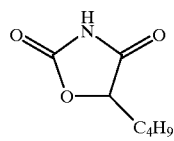
[III]-7
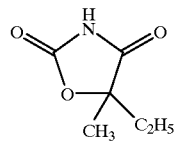
[III]-2
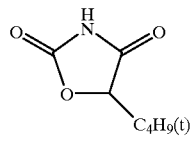
[III]-8

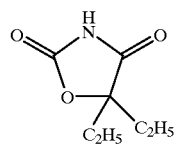
[III]-3
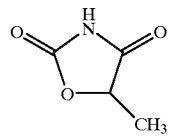
[III]-4
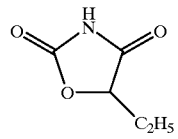
[III]-5
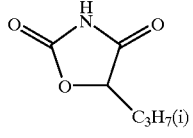
[III]-6
-continued
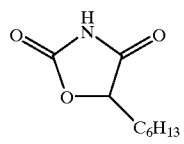
[III]-9
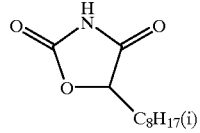
[III]-10
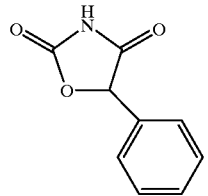
[III]-11
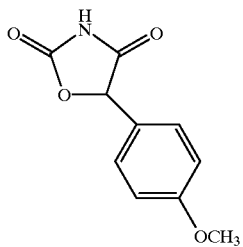
[III]-12
* * * * *